United States Patent
Taylor et al.

(10) Patent No.: US 9,963,679 B2
(45) Date of Patent: May 8, 2018

(54) CULTURED PANCREAS ISLETS

(75) Inventors: Michael J. Taylor, Mt. Pleasant, SC (US); Simona C. Baicu, Charleston, SC (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 0 days. days.

(21) Appl. No.: 13/278,492

(22) Filed: Oct. 21, 2011

(65) Prior Publication Data
US 2012/0107936 A1 May 3, 2012

Related U.S. Application Data

(60) Provisional application No. 61/405,811, filed on Oct. 22, 2010.

(51) Int. Cl.
*C12N 5/071* (2010.01)

(52) U.S. Cl.
CPC ........ *C12N 5/0677* (2013.01); *C12N 2500/00* (2013.01)

(58) Field of Classification Search
None
See application file for complete search history.

(56) References Cited

U.S. PATENT DOCUMENTS

| | | | |
|---|---|---|---|
| 5,405,742 A | 4/1995 | Taylor | |
| 5,514,536 A | 5/1996 | Taylor | |
| 5,599,659 A | 2/1997 | Brasile et al. | |
| 5,643,712 A | 7/1997 | Brasile | |
| 5,699,793 A | 12/1997 | Brasile | |
| 5,702,881 A | 12/1997 | Brasile et al. | |
| 5,723,282 A | 3/1998 | Fahy et al. | |
| 5,843,024 A | 12/1998 | Brasile | |
| 5,888,816 A * | 3/1999 | Coon et al. | 435/366 |
| 6,492,103 B1 | 12/2002 | Taylor | |
| 6,815,203 B1 * | 11/2004 | Bonner-Weir et al. | 435/377 |
| 6,994,954 B2 | 2/2006 | Taylor | |
| 7,504,201 B2 | 3/2009 | Taylor et al. | |
| 2006/0182722 A1 | 8/2006 | Hering et al. | |
| 2008/0103606 A1 | 5/2008 | Berkland et al. | |
| 2008/0227176 A1 * | 9/2008 | Wilson | 435/243 |
| 2012/0015343 A1 | 1/2012 | Taylor et al. | |

FOREIGN PATENT DOCUMENTS

| | | | |
|---|---|---|---|
| WO | WO 03/044181 A1 | 5/2003 | |
| WO | WO 03/082189 A2 | 10/2003 | |
| WO | WO 2008063465 A2 * | 5/2008 | |
| WO | WO 2010/068728 A2 | 6/2010 | |
| WO | WO 2011/110722 A1 | 9/2011 | |

OTHER PUBLICATIONS

Ricordi et al. "Automated method for isolation of human pancreatic islets", Diabetes 37: 413-420, 1988.*
Britt et al. "Neonatal pig pseudo-islets: A product of selective aggregation", Diabetes 30(7): 580-583, 1981.*
Ishizuka et al. "A culture method for the isolation of pancreatic islet cells from young rats," Pancreas 1 (6): 494-497,1986.*
Sutton, Robert, et al. "Isolation of Rat Pancreatic Islets by Ductal Injection of Collagenase1", Transplantation 42(6): 689-690, 1986.*
Mar. 7, 2012 International Search Report issued in PCT/US2011/057234.
Mar. 7, 2012 Written Opinion issued in PCT/US2011/057234.
Papas, K.K. et al., "High-Density Culture of Human Islets on Top of Silicone Rubber Membranes," Transplantation Proceedings, Oct. 1, 2005, pp. 3412-3414, vol. 37, No. 8, Elsevier Inc., Orlando, FL.
Taylor, Michael J. et al., "Islet Isolation From Juvenile Porcine Pancreas After 24-h Hypothermic Machine Perfusion Preservation," Cell Transplantation, May 1, 2010, pp. 613-628, vol. 19, No. 5, USA.
Taylor, Michael J. et al., "Hypothermic Perfusion of Pancreas: Emphasis on Preservation Prior to Islet Isolation," Methods of Bioengineering, Jan. 1, 2009.
Dec. 11, 2012 Second Written Opinion issued in International Application No. PCT/US2011/057234.
U.S. Appl. No. 12/379,239, filed Feb. 17, 2009, Taylor et al.
U.S. Appl. No. 11/075,690, filed Mar. 10, 2005, Taylor et al.
Sep. 29, 2014 Communication issued in European Application No. 11 785 177.4.
Nov. 13, 2014 Office Action issued in Australian Application No. 2011316904.
Feb. 27, 2015 Office Action issued in Chinese Application No. 201180060765.9.
Apr. 15, 2015 Office Action issued in Australian Application No. 2011316904.
Jul. 12, 2016 Decision of Refusal issued in Japanese Application No. 2013-535111.
Dec. 2, 2016 Decision of Grant issued in Japanese Application No. 2013-535111.
Aug. 4, 2017 Office Action issued in Canadian Application No. 2,815,213.
May 7, 2014 Office Action issued in Chinese Application No. 201180060765.9 (with English Translation).

* cited by examiner

*Primary Examiner* — Emily A Cordas
(74) *Attorney, Agent, or Firm* — Oliff PLC

(57) ABSTRACT

Methods of preparing pancreatic islets that may comprise pancreatites are provided. The methods may involve subjecting a pancreas and/or pieces thereof to disruption, such as, for example, an enzyme digest, and seeding the recovered cellular product comprising islets in a culture medium comprising at least a detectable amount of endocrine tissue and/or exocrine tissue.

11 Claims, 5 Drawing Sheets

Figure 4 (A-H)

CULTURED PANCREAS ISLETS

CROSS-REFERENCE TO RELATED APPLICATION

This nonprovisional application claims the benefit of U.S. Provisional Application No. 61/405,811 filed Oct. 22, 2010. The disclosure of the prior application is hereby incorporated by reference in its entirety.

GOVERNMENT SUPPORT

The invention was supported, in whole or in part, by grants from the National Institutes of Health (Grant Nos. R44DK065508 and R44DK076326). The Government has certain rights in the invention.

BACKGROUND

Type I diabetes is a widespread metabolic disorder caused by failure of beta cells of the pancreas to secrete sufficient insulin. Insulin is required for the uptake of glucose in most cell types, and inadequate insulin production causes reduced glucose uptake and elevated blood glucose levels. Without proper treatment, diabetes can be fatal. Treatment with insulin, while life-saving, often does not provide sufficient control of blood glucose to prevent the life-shortening complications of the disease, and this has given rise to intensive research into better methods of achieving and sustaining normoglycemia. Among the newer treatment strategies that have been proposed, transplantation of pancreatic beta islet cells, obtained either from other humans or animals, has received the significant attention worldwide. This is because islet cell transplantation can restore not only the insulin-secreting unit, but also the precise fine-tuning of insulin release in response to multiple neural and humoral signals arising within and beyond the islets of Langerhans.

Ever since the first experimental attempts to ameliorate Type I diabetes by transplantation of allograft donor islets the field has been challenged by the need for improved methods of retrieving and/or obtaining islets from donor pancreata. There is a considerable worldwide effort to further develop the concept for treating Type I diabetes by transplanting islets, but clinical application of the techniques developed in animal models is fraught with many challenges.

The source of the islets remains a primary concern, and isolation from donor pancreases demands resolution of questions concerning the source, supply, and condition of the donor organs. Reliance upon an adequate supply of human organs for this purpose is considered futile, such that alternative sources are actively been sought (Bonner-Weir, S. et al., New sources of pancreatic beta-cells, Nat. Biotechnol. 23:857-861, 2005; Hering, B. S. et al., New sources of pancreatic beta-cells, Nat. Biotechnol. 23:857-861, 2005; Hering, B. J. et al., Prolonged diabetes reversal after intraportal xenotransplantation of wild-type porcine islets in immunosuppressed nonhuman primates, Nat. Med., 12:301-303, 2006; Inada, A.; Bonner-Weir, S. et al., How can we get more beta cells?, Curr. Diab. Rep., 6:96-101, 2006).

Various mammals are considered optimal candidates for xenogeneic islet transplantation. Of the potential mammals, pigs are considered the donor species of choice for xenogeneic islet transplantation for a number of compelling reasons. Pigs share many physiological similarities to humans and porcine insulin has demonstrated clinical efficacy for many years. Pigs are raised as a food source and provide an ethical source of donor islets by being housed in a controlled environment to ensure safety for porcine islet xenotransplantation. However, experiences in many laboratories over the past 10 years show that isolation of porcine islets appears to be more difficult (Finke, E., et al., Large scale isolation, function, and transplantation of islets of Langerhans from the adult pig pancreas. Transplant. Proc. 23:772-773, 1991; Giannarelli, R. et al., Preparation of pure, viable porcine and bovine islets by a simple method. Transplant. Proc., 26:630-631, 1994; Marchetti, P. et al., Automated largescale isolation, in vitro function and xenotransplantation of porcine islets of Langerhans, Transplantation 52:209-213, 1991; O'Neil, J. J. et al., The isolation and function of porcine islets from market weight pigs. Cell Transplant., 10:235-246, 2001; Toso, C. et al., Isolation of adult porcine islets of Langerhans. Cell Transplant., 9:297-305, 2000), compared with the isolation of human (Kenmochi, T. et al., Improved quality and yield of islets isolated from human pancreas using two-step digestion method, Pancreas 20:184-190, 2000), bovine (Figliuzzi, M. et al., Influence of donor age on bovine pancreatic islet isolation, Transplantation, 70:1032-1037, 2000), or rodent islets (Shapiro, A. M. et al., High yield of rodent islets with intraductal collagenase and stationary digestion—a comparison with standard technique, Cell Transplant., 5:631-638, 1996).

For example, porcine islets are less compact and tend to fragment during the isolation procedure and during prolonged periods of in vitro culture (Ricordi, C. et al., A method for the mass isolation of islets from the adult pig pancreas, Diabetes, 35:649-653, 1986). Moreover, the age, and even the strain, of the donor pig has been documented by several groups to markedly influence the islet isolation process, with young, so-called market size pigs (<6 months old) proving to be particularly difficult as a source of transplantable islets (Bottino, R. et al., Isolation outcome and functional characteristics of young and adult pig pancreatic islets for transplantation studies, Xenotransplantation, 14:74-82, 2007; Dufrane, D. et al., Impact of porcine islet size on cellular structure and engraftment after transplantation: Adult versus young pigs, Pancreas 30:138-147, 2005; Toso, C. et al., Isolation of adult porcine islets of Langerhans. Cell Transplant., 9:297-305, 2000). Islets from adult pigs (>2 years old) offered not only higher yields, but retained the ability to preserve intact morphology during the isolation process and culture, in association with higher functional properties after transplantation. Despite the challenge encountered by many groups attempting to isolate islets from young pigs, donor pigs of market weight (<80 kg=<12 months old) are preferred to retired breeders (>200 kg=>2 years old) due to their abundance, lower animal and husbandry costs, and they are more suitable to meet regulatory guidelines for donor tissue for xenotransplantation. If the supply of islet cells (including but not necessarily limited to beta cells) could be augmented by culturing the donated islets from more readily available sources, which may be less compact and may or may not display a propensity for fragmenting (such as islets obtained from young pigs), in cell culture, such a new source of islets may provide sufficient material to allow a new treatment for insulin-dependent diabetes.

However, despite many efforts to improve the technique of islet isolation and preparation, the field remains constrained by the limitations and vagaries of enzymatic digestion of a gland that comprises less than 5% endocrine tissue. Consequently, harvesting islets from a single donor pancreas often yields insufficient islet mass to reverse diabetes in a recipient, such that multiple donors often have to be considered for treating a single recipient. The potential for xenotransplantation to relieve the demand on an inadequate supply of human pancreases depends upon improvements in efficacy and efficiency of techniques for isolating and preparing islets from the source pancreases (Hering, B. J. et al., The International Xenotransplantation Association consensus statement on conditions for undertaking clinical trials of porcine islet products in type 1 diabetes—executive summary, Xenotransplantation 16:196-202, 2009).

SUMMARY

The present disclosure provides novel methods for preparing a population of pancreatic islets that may comprise pancreatites, which may be heterogeneous or homogeneous, and pancreatic islets that may comprise pancreatites prepared from such methods. In embodiments, the pancreatic islets may comprise "pancreatites." In embodiments, the methods of the present disclosure comprise subjecting a pancreas and/or pieces thereof to disruption, such as, for example, an enzyme digest, and seeding the recovered cellular product comprising islets in a culture medium comprising at least a detectable amount of endocrine tissue and/or exocrine tissue, such as, for example, endocrine tissue and/or exocrine tissue obtained from a donor pancreas.

The new methods of this disclosure make it possible to obtain, prepare and/or grow islets of sufficient quality and quantity in an effort to meet the above needs (even from donor tissues yielding islets that may be immature, less compact and/or tend to fragment during the cellular product isolation procedure and during prolonged periods of in vitro culture, such as young, islets obtained from so-called market size pigs, <6 months old). The new methods of this disclosure result in novel islet compositions that may comprise structures hereinafter referred to as "pancreatites." The "pancreatites" of the present disclosure may form in culture and comprise a combination of islet (endocrine) and/or exocrine tissue.

Additional features and advantages of the present disclosure are described in, and will be apparent from, the following detailed description of embodiments.

DETAILED DESCRIPTION OF EMBODIMENTS

Figure 1:
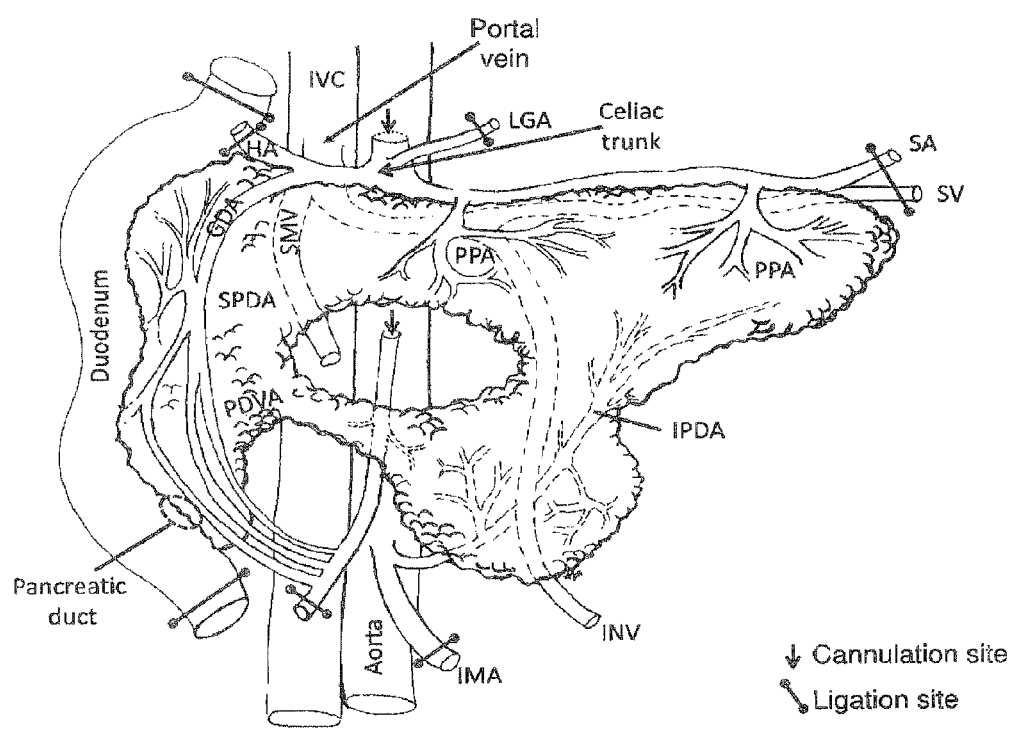
FIG. 1 is an illustration of a diagram showing the pancreas excised with a segment of the descending aorta for cannulation of the celiac trunk (CT) and superior mesenteric artery (SMA)

As used herein, the singular forms "a," "and," and "the" include plural reference unless the context clearly dictates otherwise. Thus, for example, reference to "a cell" is a reference to one or more cells and includes equivalents thereof known to those skilled in the art, and so forth.

The term "pancreatite" refers, for example, to pancreatic islet aggregates that form in culture from dispersed islets, which may be mature and/or immature, in the presence of exocrine material.

The term "small molecule" refers, for example, to nucleic acids, peptides, polypeptides, amino acids, carbohydrates, lipids, or other organic or inorganic molecules.

The term "edema" is used herein to refer, for example, to an accumulation of an excessive amount of watery fluid in cells, tissues, or serous cavities.

The terms "organ," "tissue," "donor organ," and "donor tissue" are used herein to refer to any natural or engineered organ or tissue, such as a pancreas and sections or pieces thereof.

As used herein, the term "perfusion" means the flowing of a fluid through the tissue. Techniques for perusing organs and tissues are discussed in, for example, U.S. Pat. No. 5,723,282 to Fahy et al., which is incorporated herein in its entirety.

The term "culturing" as used herein refers to maintaining cells under conditions in which they can proliferate, retain their functional state. For example, cultured islets proliferate and retain their insulin producing capacity. Cells can be cultured in growth media containing appropriate growth factors, i.e., a growth factor cocktail.

The term "autologous," when used in reference to pancreatic islets, refers to cellular product comprising islets obtained from the individual to whom the pancreatic islets that may comprise pancreatites will be administered after being cultured according to the methods of the present disclosure.

The term "heterologous," when used in reference to pancreatic islets, refers to cellular product comprising islets obtained from a different individual from the individual to whom the pancreatic islets that may comprise pancreatites will be administered after being cultured according to the methods of the present disclosure.

The present disclosure provides novel methods for preparing a population of pancreatic islets that may comprise pancreatites, which may be heterogeneous or homogeneous, and pancreatic islets that may comprise pancreatites prepared from such methods. In embodiments, the pancreatic islets may comprise "pancreatites." In embodiments, the methods of the present disclosure comprise subjecting a pancreas and/or donor tissue comprising pancreatic islets to disruption, such as, for example, an enzyme digest, and seeding the recovered cellular product comprising islets in a culture medium comprising at least a detectable amount of exocrine tissue, such as, for example, exocrine tissue obtained from a donor pancreas.

The new methods of this disclosure make it possible to obtain, prepare and/or grow islets of sufficient quality and quantity in an effort to meet the above needs (even from donor islets that are less compact and tend to fragment during the isolation procedure and during prolonged periods of in vitro culture, such as young, islets obtained from so-called market size pigs, <6 months old). The new methods of this disclosure result in novel islet compositions, which may comprise "pancreatites." The "pancreatites" of the present disclosure may form in culture and comprise a combination of islets and exocrine tissue.

This disclosure also concerns the use of the prepared pancreatic islets, which may comprise pancreatites, for implantation into an individual for in vivo therapy of diabetes. This disclosure further concerns a process of using the in vitro prepared pancreatic islets, which may comprise pancreatites, for repairing an organ in vivo to have the same functional, morphological and histological characteristics as those observed in normal pancreatic tissue. The ability to prepare, obtain and/or grow pancreatic islets, which may comprise pancreatites, in vitro opens up important new avenues for research and therapy relating to diabetes as well.

This disclosure also provides pancreatic islets that may comprise pancreatites. The pancreatic islets, which may comprise pancreatites, of the present disclosure, may be cultured and/or formed on a membrane, which may be a flat surface, such as in a flask with a silicone membrane. In embodiments, the membrane may be disposed in a conical container or a container in which the surface area of the container decreases from the top of the container to the bottom of the container. In embodiments, the membrane is a gas-permeable membrane.

This disclosure also provides pancreatic islets, which may comprise pancreatites, that, upon implantation into a recipient, may have the ability to provide much more rapid effects on the glycemic state of the recipient.

The present disclosure also describes methods whereby it is possible to prepare pancreatic islets, which may comprise pancreatites, such as functioning pancreatic islets, with histological characteristics and insulin-producing properties similar to those exhibited by natural isolated islets. The methods of the present disclosure may be employed to produce a stock of pancreatic islets that may comprise pancreatites, for use in experimental investigations or therapeutic islet transplantation. In embodiments, a large numbers of pancreatic islets that may comprise pancreatites, may be produced by the present method from relatively small quantities of pancreatic tissue. In embodiments, the pancreatic islets, which comprise pancreatites, and cellular materials obtained as a result of carrying out the methods of the present disclosure may be employed to yield further generations of pancreatic islets, which may comprise pancreatites, (i.e., in embodiments, the pancreatic islets, which may comprise pancreatites, are self-reproducing. The present method may therefore provide a means whereby large quantities of experimentally-useful pancreatic islets, which comprise pancreatites, may be produced. Further, in view of the properties of the pancreatic islets that may comprise pancreatites, the methods disclosed herein may be employable in clinical applications to provide a source of pancreatic islets for therapeutic islet transplantation or research.

In embodiments, the pancreatic islets that may comprise pancreatites may be prepared from cellular product comprising islets obtained from one or more fresh, frozen, or cryogenically treated donor pancreas. In embodiments, cellular product comprising islets may comprise immature islets, mature islets or a mixture thereof. In embodiments, the pancreatic islets that may comprise pancreatites may be prepared from cellular product comprising islets obtained from any animal, such as mammals. Suitable mammalian subjects include rodents such as, for example, mice, rats, guinea pigs, and rabbits, non-rodent mammals such as, for example, pigs, dogs, cats, sheep, horses, cows, and goats, primates such as, for example, chimpanzees and humans. In embodiments, cellular product comprising islets may be obtained from a fetal donor, neonatal donor, or juvenile donor.

The pancreatic islets, which may comprise pancreatites, prepared by the methods of the present disclosure may be used for a number of assays. In embodiments, the pancreatic islets that may comprise pancreatites, may be used, for example, to screen and evaluate insulinotropic compounds, drugs, other large molecules or small molecules. In another embodiment, the pancreatic islets that may comprise pancreatites, may be used, for example, to measure insulin content, and to analyze insulin biosynthesis. In embodiments, the pancreatic islets that may comprise pancreatites prepared by the method of the present disclosure may be used to characterize the effects of a small molecule or drug compound on second messenger activity (e.g., cAMP, inositol triphosphate (IP, calcium)). A further embodiment of the present disclosure relates to the use of pancreatic islets that may comprise pancreatites, to measure the metabolites of islet cells. In addition, the pancreatic islets that may comprise pancreatites, prepared by the methods of the present disclosure, may be utilized to measure glucagon and somatostatin release and the regulation of glucagon and somatostatin by various small molecules and drug compounds.

In embodiments, the methods of preparing pancreatic islets that may comprise pancreatites comprises seeding cellular product comprising islets on a culture medium. In embodiments, the culture medium is present on a membrane, which may be located in a container, such as, for example, a culture flask. In embodiments, the membrane is a silicone membrane, which may be gas permeable. In embodiments, the membrane is a flat membrane, which may or may not be gas permeable. In embodiments, the membrane is a gas permeable membrane. In further embodiments, the culture medium is present in a polycarbonate gas-permeable silicone membrane culture flask.

In embodiments, methods of preparing of pancreatic islets that may comprise pancreatites, may comprise culturing cellular product comprising islets on a membrane, which may be flat, such as, for example, a silicone membrane. In embodiments, the culture medium is present on the membrane, which optionally is located in a culture flask. In embodiments, the membrane is a silicone membrane, which may be gas permeable. In embodiments, the membrane is a flat membrane, which may or may not be gas permeable. In embodiments, the membrane is a gas permeable membrane. In further embodiments, the culture medium is present in a polycarbonate gas permeable silicone membrane culture flask.

In embodiments, methods of preparing of pancreatic islets that may comprise pancreatites, may comprise culturing cellular product comprising islets in gas permeable cultureware flask manufactured by Wilson Wolf Manufacturing (Wilson Wolf Manufacturing Inc., MN). In embodiments, gas permeable cultureware flask comprises a silicone membrane and the cellular product comprising islets is, for example, obtained from an animal, such as mammal, such as a human or pig. In embodiments, cellular product comprising islets may be obtained from a fetal donor, neonatal donor, or juvenile donor.

The method of the present disclosure may utilize dispersed cellular product comprising islets and thus, generally all isolated cellular product comprising islets may be used. Thus, the method of the present disclosure avoids manual selection of islets and therefore, saves considerable time on sample preparation.

The method of the present disclosure provides an improvement over currently used islet preparation methods, and markedly increases the efficiency of islet preparation.

In embodiments, the method further comprises contacting the cellular product comprising islets and/or the pancreatic islets that may comprise pancreatites, with an antioxidant, such as, for example, TROLOX® (an analogue of α-tocopherol; in a range of from about 30 to about 80 µM, such as about 50 µM), Q-VD-OPH (a broad spectrum caspase inhibitor; in a range of from about 5 to about 20 µM, such as about 10 µM), hepatocyte growth factor, kaposis fibroblast growth factor, nicotinamide, or a combination thereof.

In embodiments, kits for the preparation of pancreatites are provided. In one embodiment, the kit may comprise, for example, digestion enzymes, a culture flask with a membrane (as discussed above) and a culture medium. In another embodiment, the kit may also include, for example, membranes and perfusate solutions for preservation of the donor tissues prior to isolation of the cellular product comprising islets.

In embodiments, a method of preparing pancreatic islets, which may comprise pancreatites, is provided. In embodiments, the method comprises culturing a cellular product comprising islets on a membrane to prepare and/or obtain pancreatic islets that may comprise pancreatites. In embodiments, the cellular product comprising islets further comprises an exocrine substance. In embodiments, cellular product comprising islets does not include any exocrine substance. In embodiments, the exocrine substance is added to the culture medium separately (i.e., separate from the cellular product comprising islets). For example, in embodiments, the exocrine substance may be added to the culture medium either before or after the cellular product comprising islets (which may or may not include any exocrine substance) is added to the culture medium.

In embodiments, a method of islet transplantation is provided. For example, in embodiments, the method of islet transplantation comprises culturing a cellular product comprising islets on a membrane to obtain pancreatic islets that may comprise pancreatites, and administering to a recipient, such as a mammal, the pancreatic islets that may comprise pancreatites. In embodiments, the cellular product comprising islets further comprises an exocrine substance. In embodiments, cellular product comprising islets does not include any exocrine substance, and the exocrine substance is added separately. For example, in embodiments, exocrine substance may be added to the culture medium either before or after the cellular product comprising islets (which may or may not include any exocrine substance) is added to the culture medium. In embodiments, administration may be to a diabetic recipient, such as a diabetic mammal. In embodiments, the membrane is a silicone membrane that may be gas permeable. In embodiments, the membrane is a flat membrane that may or may not be gas permeable. In embodiments, the membrane is a gas permeable membrane. In further embodiments, the culture medium is present in a polycarbonate gas permeable silicone membrane culture flask.

In embodiments, administration of the pancreatic islets, which may comprise pancreatites, may be by implantation under a kidney capsule of the mammal, subcutaneous, intravenous, via a liver portal vein, or into the pancreatic parenchyma. In embodiments, the pancreatic islets, which may comprise pancreatites, are administered to a recipient, which is a mammal, such as a human. In yet other embodiments, the administered pancreatic islets, which may comprise pancreatites, are autologous or heterologous.

The method of forming pancreatic islets of the present disclosure may include a method of isolating cellular product comprising islets, a culture medium that may be tailored for pancreatic islet cells, and a method of culturing the cellular product comprising islets to prepare pancreatic islets that may comprise pancreatites, and results in improved quantities of cellular product comprising islets being isolated from a given quantity of donor tissue and improved islet function and viability. The pancreatic islets, which may comprise pancreatites, and methods of the disclosure, may allow for enhanced transplant capabilities for pancreatic islets, and increased transplantation success.

The excision of the donor pancreas (or pancreatic donor tissue) prior to isolating the cellular product comprising islets means that ischemia of the donor pancreas (or pancreatic donor tissue) is total and inevitable even though the period may be brief. An immediate consequence of cessation of blood supply to of the donor pancreas (or pancreatic donor tissue) is deprivation of the supply of oxygen to the donor tissues, but anoxia (total) or hypoxia (partial) is only one of the many consequences of a lack of blood supply. A multifactoral cascade of events ensues following the initiation of ischemia. The pivotal event is ATP depletion, which occurs within the first few minutes of oxygen deprivation. This early event leads immediately to a shift from aerobic to anaerobic metabolism, which very quickly becomes self-limiting with the production of lactate and protons. Cell depolarization also occurs very early in the cascade leading to a breakdown of ion homeostasis, and a concatenation of other intracellular and membrane-associated events that eventually culminate in cell death by either apoptosis or necrosis. Preventing such destructive pathways, prior to beginning the procedures for isolation of the cellular product comprising islets, increases the quality and quantity of cellular product comprising islets that may be harvested from a given pancreas or section thereof.

The basic principle of cellular preservation for clinical application is to minimize the deleterious effects of ischemia and anoxia during the preservation interval. This can either be achieved pharmacologically by using a wide variety of cytoprotective drugs, and/or by reducing temperature. Interestingly, conventional wisdom teaches us that there is no single drug, or cocktail of drugs, that can so safely and effectively suppress metabolism and provide ischemic protection for multiple tissues and organs as the application of hypothermia can. Accordingly, the focus changes to control the environment of cells to optimize hypothermic preservation.

In embodiments, the methods disclosed herein implement an approach that utilizes advances in perfusion technology and optionally combines those advances with hypothermic blood substitute solutions to improve $O_2$-delivery by means of PFC-augmentation. This approach circumvents several recognized shortcomings in the present modes of clinical pancreas storage, the most notable of which is the demonstrated low penetration of PFC and oxygen using the conventional two layer method (TLM).

In the specific case of pancreas preservation prior to isolation of cellular product comprising islets, a salutary effect of hypothermic machine perfusion (HMP) on islet yield in a juvenile porcine model has emerged. However, given the vulnerability of islets to even short periods (<10 h) of cold ischemia, the approaches described herein extend tolerance to ischemia by circumventing the constraints recognized in conventional techniques of pancreas preservation and allow for an increased yield of cellular product comprising islets and thus an increased quantity and quality of pancreatic islets that may comprise pancreatites.

In embodiments, cellular product comprising islets that is to be cultured to form pancreatic islets that may comprise pancreatites, may be isolated by application of HMP and the development of interstitial edema while preserving the integrity of the islets, which may greatly increase the amount and quality of cellular product comprising islets that may be retrieved compared with conventional methods applied to nonperfused donor tissues (i.e., fresh or static cold stored donor tissues). In embodiments, an enzyme digestion may be employed in order to further assist the isolation of the cellular product comprising islets.

In embodiments, the cellular product comprising islets to be used as a starting material may be obtained by generally known methods for obtaining functional islets from mammalian pancreas containing islet bodies, i.e. from fetal, neonate or adult pancreas. Such methods may comprise comminuting the whole pancreas or a portion thereof and subjecting the comminuted pieces to digestion by exposing them to a solution of an enzyme that lysed connective tissue e.g. collagenase, hyaluronidase, trypsin, and mixtures thereof, for a period sufficient to liberate the islets from the surrounding pancreatic tissue. In embodiments, the comminuted pieces are subjected to only very mild digestion, e.g. so that the degree of tissue lysis corresponds approximately to that obtained from digestion with a collagenase solution containing about 750 collagenase Units per ml for about 12 to 15 minutes at about 37° C. For example, the comminuted pancreatic pieces may be subjected to the enzyme by methods, such as, for example, perfusion of the enzyme solution into the donor tissue, and/or by shaking the donor tissue while in contact with the enzyme solution. In embodiments, the donor tissue may be in contact with the enzyme solution for any desired amount of time, such as, for example, only the minimum of time required to liberate a substantial number of islets. In embodiments, dilute solutions of the enzymes may be used, e.g. with a tissue lysing potency no greater than that of a reference solution containing about 1,500 Units of collagenase per ml, such as about 1000 Units/ml, or about 750 Units/ml. In embodiments, the methods of the present disclosure may use milder connective tissue-lysing enzymes, such as collagenase and/or hyaluronidase, rather than the more harshly-acting enzymes, such as trypsin, which are known to disassociate cells. In embodiments, the Roche MTF enzyme may be used.

In embodiments, the cellular product comprising islets that is to be cultured to form pancreatic islets, which may comprise pancreatites, may be isolated by methods comprising developing edema during perfusion of the donor pancreas and/or sections or pieces thereof (donor tissue). In such embodiments, developing edema during perfusion of the donor tissue may occur by increasing a first flow rate of the perfusion solution through the tissue to achieve a second flow rate, increasing a first perfusion pressure applied by the perfusion apparatus to the tissue to achieve a second perfusion pressure, and/or selecting a composition of the perfusion solution that causes edema of the tissue.

In embodiments, development of edema may occur by increasing a first flow rate of the perfusion solution through the donor tissue to achieve a second flow rate, increasing a first perfusion pressure applied by the perfusion apparatus to the donor tissue to achieve a second perfusion pressure, and/or selecting a composition of the perfusion solution that causes edema of the donor tissue, where the extent of edema may be assessed by monitoring buoyancy of the donor tissue, monitoring surface area of the donor tissue, monitoring a circumference of the donor tissue, monitoring weight and/or mass of the donor tissue, and or monitoring volume of the donor tissue.

In embodiments, cellular product comprising islets that is to be cultured to form pancreatic islets, which may comprise pancreatites, may be isolated by methods comprising providing a tissue having desired cells that are less prone to destructive freezing and undesired cells that are more prone to destructive freezing, freezing the tissue, disrupting the tissue, warming the tissue, and separating the desired cellular product comprising islets from undesired cellular material to obtain the cellular product comprising islets.

In embodiments, the cellular product comprising islets that is to be cultured to form pancreatic islets that may comprise pancreatites, may be isolated by methods comprising surgically preparing an ex vivo tissue for vascular and ductal cannulation, cooling the tissue, equilibrating tissue with a cryoprotective agent, optionally freezing the tissue to a temperature from about −10° C. to about −200° C., optionally mechanically disrupting the tissue while keeping the tissue frozen, optionally thawing the tissue, filtering the tissue, washing the tissue, purifying the cellular product comprising islets, such as by gradient purifying.

In embodiments, cellular product comprising islets that is to be cultured to form pancreatic islets that may comprise pancreatites, may be isolated by methods comprising infusing islet tissue with a cryoprotectant solution comprising a cryoprotective agent (CPA) via a vascular system, infusing the acinar tissue with an aqueous solution via a ductal system, freezing the pancreas, disrupting the pancreas, warming the pancreas, and separating the islets. In embodiments, cellular product comprising islets may retain sufficient functional integrity to be useful as a transplantation resource.

Hypothermic Machine Perfusion (HMP): Conventional methods of organ preservation for transplantation rely principally upon static cold storage on ice, a relatively simple and economic technique that has been used for several decades. However, in the field of pancreas preservation, particularly as it applies to source organs for isolation of cellular product comprising islets, static cold storage imposes severe restrictions upon the yield and quality of islets obtained from a single donor pancreas. For example, introducing a perfluorochemical layer to purportedly increase the supply of oxygen to the ischemic organ has failed in static cold storage methods to provide the added protection.

In embodiments, the cellular product comprising islets that is to be cultured to form pancreatic islets that may comprise pancreatites, may be isolated from a donor tissue that is preserved by methods utilizing a combination of technologies in HMP and Hypothermic blood substitutes (HBS) along with PFC oxygenation.

Hypothermic blood substitutes as preservation media: Traditionally, a variety of organ preservation solutions have been developed.

U.S. Pat. Nos. 5,643,712, 5,699,793, 5,843,024 to Brasile and U.S. Pat. Nos. 5,599,659, 5,702,881 to Brasile et al., the disclosures of each of which are incorporated herein by reference in their entireties, describe separate resuscitation and preservation solutions for tissues and organs. The Brasile patents disclose compositions that may be used in methods of this disclosure.

Taylor et al. have formulated and evaluated two solutions designated HYPOTHERMOSOL™-purge (HTS-P) and HYPOTHERMOSOL™-maintenance (HTS-M). Some aspects of these solutions are described in U.S. Pat. Nos. 5,405,742 and 5,514,536 to Taylor, the disclosures of both of which are incorporated herein by reference in their entireties. The Taylor patents disclose compositions that may be used in methods of this disclosure.

The protective properties of solutions such as the UNISOL® family of solutions (as described in U.S. Pat. Nos. 6,492,103 and 6,994,954, entitled "System for organ and tissue preservation and hypothermic blood substitution" to Taylor, the disclosures of which are hereby incorporated by reference in their entireties) may be used in methods of this disclosure. In embodiments, UNISOL® may be utilized as the vehicle solution for emulsifying PFCs to significantly increase its oxygen delivery capacity, in addition to cytoprotective additives.

In embodiments, the principal solution may be a hyperkalemia, "intracellular-type" solution designed to "maintain" cellular integrity during hypothermic exposure at the nadir temperature (<10° C.).

Increasing oxygen delivery to tissues during hypothermic storage and the role of PFCs: The UNISOL® "maintenance" solution was developed and tested at temperatures in the range of 7-10° C., which conforms with the temperature range in which ATP reserves can be re-established if an adequate supply of $O_2$ is maintained by continuous perfusion. For example, numerous investigations have suggested that oxygen supply is essential during hypothermic preservation of livers.

The rapid depletion of adenine nucleotides during cold storage of organs at 0-2° C. (e.g. conventional static cold ice-storage) may be suggestive that mitochondrial function is severely impaired by hypothermia. These levels of $O_2$ may need to be sustained during perfusion to ensure the highest quantify and quality cellular products comprising islets, and the use of PFCs allows for this to be accomplished.

PFCs are hydrocarbons in which all or most of the hydrogen atoms are replaced with fluorine (e.g., perfluorocarbon). They have twice the density of water and a high capacity for dissolving respiratory gases. The solubility of dissolved oxygen in PFC is approximately 25 times greater than in blood or water. The ability of PFCs to release oxygen in accordance with Henry's Law is not significantly influenced by temperature, making them ideal for delivering oxygen during hypothermic organ preservation. This is also supported by recent demonstrations that the gas-dissolving and gas-unloading properties of perfluorocarbon were necessary in a peritoneal perfusion application for systemic oxygenation since the same effect was not obtained when saline solution alone was employed as the perfusate. However, the use of perfluorocarbon under hypothermic conditions has been limited.

The application of one or more of these pancreas or donor tissue preservation strategies minimizes damage and cell death in the donor tissue or organ, which may promote an increase in the overall cellular product comprising islets yield and thus promote an increase in the overall yield of pancreatic islets that may comprise pancreatites.

As discussed above, procurement and preservation of pancreata is important for isolation of cellular product comprising islets as a prelude to culturing a cellular product comprising islets on a membrane to obtain pancreatic islets that may comprise pancreatites and the eventual transplantation of the pancreatic islets that may comprise pancreatites as an option for the treatment of Type I diabetes mellitus. Pancreas perfusion can further be applied for the preservation of organs exposed to warm ischemia prior to isolation of cellular product comprising islets and to optimize pancreas preservation solution for a better yield and quality.

Physiologically, the pancreas is a low flow organ. In embodiments, during and/or prior to isolation of the cellular product comprising islets, the methods of this disclosure may comprise pancreas perfusion, which may be based on a low constant pressure (about 10 mmHg or less, such as from about 1 mmHg to about 10 mmHg) driven flow. The present design of the LIFEPORT® may not accommodate infusion pressures of less than 10 mmHg. Thus, lower pressure values may be installed in order to reach the desired infusion pressures of less than 10 mmHg for the methods disclosed herein for preserving pancreata for isolation of the cellular product comprising islets. In embodiments, the driven flow rate values may be selected in accordance with the desired cellular product comprising islets characteristics and quality (such as warm ischemia exposure, size, species, etc.).

In embodiments, the methods of perfusion may be based on a high (about 10 mmHg or more, such as from about 10 mmHg to about 60 mmHg) constant pressure driven flow.

In embodiments, the methods described herein employ an apparatus for perfusing one or more pancreatic organs or tissue (hereinafter generally referred to as donor tissues). An exemplary apparatus is described in U.S. patent application Ser. No. 12/379,239, which is a division of U.S. patent application Ser. No. 11/075,690, filed Mar. 10, 2005 (issued as U.S. Pat. No. 7,504,201 on Mar. 17, 2009) the entire disclosures of which are hereby incorporated by reference in their entireties. In embodiments, the methods described herein employ the LIFEPORT® platform transporter or a modified LIFEPORT® platform transporter in order to accomplish hypothermic machine perfusion (HMP) of a donor tissue (i.e., the pancreas).

In embodiments, HMP may result in uniform fluid accumulation within the donor tissue that in turn may provide a disrupted extracellular space with beneficial effects for cellular product comprising islets isolation without compromising islet viability and function of the islets. In embodiments where an enzyme digestion is employed, such disruption may allows the enzyme digestion to proceed more efficiently and thus reduces the required time necessary to isolate the cellular product comprising islets. The methods of this disclosure, described herein with respect to juvenile porcine pancreata, may be easily applied to human and other donor pancreases. In embodiments, pancreas hypothermic perfusion optimization may be achieved for development of methods of organ evaluation and quality control during perfusion in order to reliably select pancreases for isolation of cellular product comprising islets.

In embodiments, the LIFEPORT® machine for pancreas perfusion may be adapted to operate a flow rate of less than 150 ml/min, such as less than 100 ml/min, or from about 10 ml/min to about 100 ml/min, such as from about 15 ml/min to about 50 ml/min, or from about 20 ml/min to about 30 ml/min.

In embodiments, the LIFEPORT® machine for pancreas perfusion may be adapted to operate at a high pressure setting (about 10 mmHg or more, such as in the range from about 10 mmHg to about 60 mmHg, or in the range from about 20 mmHg to about 50 mmHg)-controlled perfusion of porcine pancreas as a prelude to pancreas processing for isolation of cellular product comprising islets. In embodiments, the LIFEPORT® machine for pancreas perfusion may be adapted to operate a flow rate of less than 200 ml/min, such as less than 150 ml/min, or from about 10 ml/min to about 150 ml/min, such as from about 50 ml/min to about 120 ml/min, or from about 60 ml/min to about 110 ml/min.

Embodiments of the disclosure may provide an improved method of isolating cellular products comprising islets (optionally in combination with enzyme digestion), which may be more consistent and reliable than conventional methods that are based on enzyme digestion. Embodiments may also provide methods that yield an optimum quantity of desired cellular products comprising islets.

In embodiments, development of edema in donor tissues to form a swelled tissue may occur by application of hypothermic machine perfusion (HMP). The application of donor tissue HMP (the pancreas HMP), as a prelude to isolation of cellular products comprising islets also capitalizes upon the some of benefits of HMP demonstrated for other various organs (principally the kidney) as a means of better preservation during extended periods of storage, especially for suboptimum organs.

The progressive development of edema during extended machine perfusion of organs is a phenomenon that is generally regarded as undesirable. Contrary to expectations, development of edema, such as up about 280% (i.e., a 180% gain in the particular parameter that is monitored to assess the extent of edema, such as, for example, weight, mass, circumference, buoyancy, and/or volume), or up to about 250%, or up to 150% to did not prove deleterious to cellular product comprising islets harvesting, but was observed to be of considerable benefit by correlating with a more efficient disruption of the pancreas during enzymatic digestion to yield a significantly greater number of cellular products comprising islets.

In embodiments, developing edema during perfusion of the donor tissue to form a swelled tissue may result in a swelled tissue exhibiting a weight, mass, circumference, surface area, buoyancy, and/or volume about 110% (i.e., gain in weight, mass, circumference, surface area, buoyancy, and/or volume of about 10%) of that of the initial or original nonperfused donor tissue, such as from about 120% to about 280% (i.e., gain in weight, mass, circumference, surface area, buoyancy, and/or volume of from about 20% to about 180%), or from about 130% to about 250% (i.e., gain in weight, mass, circumference, surface area, buoyancy, and/or volume of from about 30% to about 150%).

It is believed the presence of a predetermined amount of edema causes sufficient disruption to the extracellular matrix and architecture of the pancreas or pancreatic tissue that the subsequent distension and digestion of the gland proceeds more effectively. This is evidenced by significantly shorter digestion times, a more homogeneous digestion product. The structure and function of the cellular products comprising islets per se did not appear to be compromised by the level of tissue edema encountered in these studies. Concerns that a change in the hydration of the isolated cellular products comprising islets due to HMP might alter the buoyant density of the islets and thereby alter their ability to be separated from any undesired exocrine tissue on a density gradient did not appear to be a problem. This may presumably be due to the fact that any inherent edema in the islets is counteracted by the pregradient incubation in UW solution, which is a hypertonic medium that would dehydrate the islets during the 30-min cold incubation prior to loading on the density gradient for purification, which is generally used in islet isolation protocols (Lakey, 3. R. T., Technical aspects of islet preparation and transplantation, Transpl. Int., 16:613-632, 2003; Lakey, J. R. T.; Current human islet isolation protocol, Chuo-ku, Osaka: Medical Review Co. Ltd., 2004; the disclosures of which are hereby incorporated by reference in their entireties).

The unanticipated benefit of HMP described above may be achieved without compromising the quality of the harvested cellular product comprising islets. These effects and standards of preservation may be achieved using either of two proprietary solutions, KPSI and UNISOL® UHK.

Further improvements and benefits to this technique may occur by optimizing the composition of these baseline perfusates by adding cytoprotective agents design to minimize preservation and reperfusion injury, and/or PFCs. For example, cytoprotective additives may be additives displaying efficacy during low temperature preservation and therefore a high probability they will have a positive impact on the quality of pancreas preservation during hypothermic machine perfusion, such as antioxidants, anti-apoptotic agents and trophic factors.

In embodiments, the donor tissue may be divided into smaller pieces, fractured, and/or fragmented. In order to enhance fracturing of a donor tissue, such as the pancreas, volumetric warming may be combined with the addition of a compressed-air heat exchanger immersed in a hot water bath. In embodiments where the donor tissue is cooled or frozen on a preservation or transport platform, this may enable thawing of the donor tissue without the need to remove it from the platform. Donor tissue dividing or fracturing may occur at any time before exposure to the digestive enzyme, such as during warming of the donor tissue.

In embodiments, it may be advantageous to expose the donor tissue to various doses of digestive enzyme(s), such as those mentioned above and those commercially available, in the to assist in connective tissue dispersion to allow release of the cellular product comprising islets (which optionally may be cryoprotected islets) from the disrupted tissue.

In embodiments, after the extent of edema has reached a predetermined level, such as a level of edema where the there is gain in weight, mass, circumference, surface area, buoyancy, and/or volume of up to about 200% (i.e., if the initial or original weight, mass, circumference, surface area, buoyancy, and/or volume of the tissue is X (such as 100 grams), a gain of about 200% would result in a final weight of 3X (300 grams), such as a gain of up to about 150%, or a gain of up to about 100%, the donor tissue may be disrupted to release cellular product from the disintegrated donor tissue. In embodiments, disrupting the donor tissue may occur while the donor tissue is frozen, while the donor tissue is warming, and/or after the tissue reaches room temperature. In embodiments, the disruption may be achieved by mechanical stress, thermo-mechanical stress induced by differential expansion, thermo-mechanical stress induced by steep temperature gradients, and thereto-mechanical stress induced by volume change upon freezing, via a digestive enzyme, or a combination thereof.

Thermo-mechanical stress may be the outcome of the tendency of material to contract upon freezing, which may be driven by three different effects: volume change upon freezing as described above, steep temperature gradients, and differential expansion in composite materials. In practice, two or more of the above effects may be acting in concert.

In other embodiments, disrupting the donor tissue may be achieved by mechanically fracturing a frozen donor tissue. For example, this may be accomplished in two stages. The first stage may be to physically split the frozen donor tissue into pieces, for example, with a hammer and chisel. The second stage may be to grind the frozen tissue pieces while immersed in warm water or isotonic medium, for example, by using an electric ice crusher or blender. This may also serve to effect rapid warming and dilution of a cryoprotectant, if included, at the same time as mechanically grinding the tissue.

In embodiments, the method further comprises separating the cellular product comprising islets from the undesired donor tissue material. In embodiments, the islets are present in an amount greater than about 20% of the total area of exocrine tissue and endocrine tissue present in the culture medium, such as in an amount greater than about 40%, or in an amount greater than about 60%, or in an amount greater than about 80% of the total area of exocrine tissue and endocrine tissue present in the culture medium, wherein the amount of islets is calculated by the ratio of the area encompassed by the islets to the total area of exocrine tissue and endocrine tissue present in the culture medium. In embodiments, the islets are present in an amount less than about 70% of the total area of exocrine tissue and endocrine tissue present in the culture medium, such as in an amount less than about 60% or 50% of the total area of exocrine tissue and endocrine tissue present in the culture medium, wherein the amount of islets is calculated by the ratio of the area encompassed by the islets to the total area of exocrine tissue and endocrine tissue present in the culture medium. In embodiments, the exocrine substance is present in an amount greater than 60% of the total area of exocrine tissue and endocrine tissue present in the culture medium such as in an amount greater than about 70%, or in an amount greater than about 80% or in an amount greater than about 90% of the total area of exocrine tissue and endocrine tissue present in the culture medium, wherein the amount of exocrine substance is calculated by the ratio of the area encompassed by the exocrine substance to the total area of exocrine tissue and endocrine tissue present in the culture medium.

In other embodiments, the cellular product comprising islets may comprise an exocrine substance in any desired amount, such as an amount less than 10%, such as from about 0.5% to about 10%, such as from about 1% to about 8%, or from about 2% to about 5%. In alternative embodiments, cellular product comprising islets is separated from the exocrine substance and thus does not include any exocrine substance. Separation of the cellular product comprising islets may be achieved, for example, by filtration, density gradient separation, tissue culture, or a combination thereof. Filtration may be performed using a filtration apparatus, such as a stainless steel mesh (tea strainer). Separation may include washing the filtered donor tissue with a medium containing a protease inhibitor, such as PEFABLOC®, and a deoxyribonuclease, such as PULMOZYME®, such that harmful endogenous proteases and DNA from lysed exocrine tissue are removed. In embodiments, the filtered donor tissue may be stained with an indicator for identifying the cellular product, such as dithizone for staining islets, and examined under the microscope for the presence of intact cellular product comprising islets.

The separated cellular product comprising islets may not be cleanly cleaved from the donor tissue and not all of the cellular product comprising islets may be completely intact. For example, with respect to islets, some islet tissue may have a diffuse or loose structure that could reflect osmotic shock due to direct immersion into an aqueous medium during any warming of a frozen pancreas. In embodiments, such a problem may be averted by employing osmotic buffering during elution of the CPA from the islet tissue during or after thawing of a frozen pancreas. Utilizing the osmotic buffering technique in embodiments may protect the structure of the islet tissue and minimize osmotic swelling and lysis during efflux of the permeating CPA. In contrast, in such embodiments, osmotic buffering does not impact the simultaneous destruction and lysis of the acinar cells because these cells have not been protected by CPA permeation.

In embodiments, cellular product comprising islets may be isolated according to the method of Ricordi et al. (An automated method for the isolation of human pancreatic islets, Diabetes, 1988; 37:413) or other means familiar to those of skill in the art.

In embodiments, the cellular product comprising islets is added to culture medium as disclosed herein or familiar to those of skill in the art, cultured for suitable time periods to maintain or enhance functionality and viability, and introduced into the recipient by any suitable means known in the art, for example, infusion into the liver via a portal vein.

In embodiments, cellular product comprising islets may be cultured for periods of about 3 hours to about 4 weeks or more, such as from about 24 hours to about 14 days, such as from about 4 days to about 10 days. However, cellular product comprising islets may be able to be cultured using the present compositions and methods for 60 days or even longer.

In embodiments, the culture medium may be any liquid composition capable of sustaining mammalian cell growth. A large range of suitable liquid culture media are available commercially. The cell-growth promoting qualities of any given liquid medium may of course be readily determined by trial and experiment by conducting trial culturings, e.g. with isolated pancreatic islets and determining whether cell aggregation, proliferation, multiplication and/or growth occurs.

In embodiments, the culture medium comprises a base medium suitable for the cultivation of mammalian cells, such as ones sold under the CELLGRO® trademark or available from Mediatech, Inc.; including, for example, CMRL 1066, to which effective amounts of nicotinamide, vitamin E and HSA are added. Other equivalent base media may be used in place of CMRL including, but not limited to, Basal Media Eagle (BME), DMEM; DMEM/F12, Medium 199; F-12 (Ham) Nutrient Mixture; F-10 (Ham) Nutrient Mixture; Minimal Essential Media (MEM), Williams' Media E; RPMI 1640, $CO_2$ independent medium and mixtures thereof. (These formulations are available from GIBCO® BRL/Life Technologies, Inc., Gaithersburg, Md. and other commercial sources). Persons of skill in the art will appreciate that many other suitable base media are commercially available, or can be routinely formulated in the laboratory. In general, such base media contain inorganic salts (e.g. NaCl, KCl, $NaH_2PO_4$, $CaCl_2$, $MgSO_4$, Na acetate), naturally occurring amino acids, vitamins, buffers and additional components as may be advantageous (cholesterol, coenzyme A, glucose glutathione, Thymidine, Uridine-5 triphosphate, antibiotics), as needed to support the viability of cells.

In embodiments the medium may additionally comprise other components, such as, for example, ITS liquid media, ITS+Premix, ciprofloxacin hydrochloride, insulin, transferrin, selenium, water soluble linoleic acid, sodium pyruvate, zinc sulfate or zinc chloride, Hepes, N-acetyl cystine, nicotinamide, heat inactivated porcine serum, L-glutamine, heparin sodium, TROLOX®, Q-VD-OPH, PUL-MOZYME® and GLUTAMAX™ 1.

An exemplary preparation of a culture medium may comprise: a base medium of Supplemented ME 199 (1000 ml) [CELLGRO® 99-601-CM], which has been prepared by additionally adding 50 ml sodium pyruvate (100 ml stock), adding 1 ml zinc sulfate (4.8 mg/ml stock), adding 10 ml ITS liquid media, adding 2 ml of Ciprofloxacin Hydrochloride (10 mg/ml stock), adding 60 mg N-acetyl cystine, adding 1.22 g Nicotinamide (final 10 mM). To such a culture medium the following steps may occur relatively close to the time of use: adding 100 ml heat inactivated porcine serum, adding 25 ml L-glutamine (200 mM stock), adding 10 ml Heparin sodium (1000 U/ml stock), adding 14 ml PUL-MOZYME® (2500 U/2.5 ml ampule), adding TROLOX®* (final concentration of 50 µM), and adding Q-VD-OPH* (final concentration of 10 µM).

In embodiments, small quantities of glucose may be added to the medium in concentrations corresponding to those occurring in the vivo pancreas e.g. molar concentration of glucose of about 5 to about 20 mM, such as about 10 mM, and the culture medium may be equilibrated before use with air containing about 5% $CO_2$ to achieve partial pressures of dissolved gases corresponding to the in vivo condition. In embodiments, the medium contains effective concentrations of antibiotics e.g. about 50 to about 200 µU/ml, such as about 100 µU/ml of penicillin and about 50 to about 200 µg/ml, such as about 100 µg/ml streptomycin to inhibit growth of undesired microorganisms. In embodiments, the medium may also have added to it small quantities of mammalian serum which contains proteins that promote attachment of cell tissues to culture substrates. For example, the serum may be present in an amount of about 5 to 20% by volume, such as about 15% by volume, based on the volume of the mixture and is heterologous with respect to the cellular product comprising islets undergoing culture.

In embodiments, the culture medium may be maintained under conditions approximating to the vivo condition that are considered to be adapted to sustain mammalian cell growth, i.e. at approximately normal mammalian body temperatures in the range of from about 35° to 40° C., such as at about 37° C. and under an atmosphere of a suitable gas composition, such as about 5% $CO_2$/95% air adapted to maintain partial gas pressures in solution. In embodiments, the culture is maintained in a water-saturated atmosphere to avoid undesirable concentration changes in the medium through evaporation losses.

Important constituents of the gas phase may include oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1-10% in the incubator. In embodiments, the $CO_2$ concentration may be about 5%.

In embodiments, after the initial seeding of the cellular product comprising islets in the culture medium, the medium may be changed at frequent intervals in order to maintain effective nutrient and antibiotic levels in the medium and to wash away any contaminants. For example, for the first 3 or 4 days the medium may be changed at intervals of about 12 to 24 hours. For cultures lasting for a period of time longer than 3 or 4 days, the medium may be changed at longer intervals, such as from about 5 to about 10 days.

In embodiments, the density of islets that may be introduced into the culture medium may be varied. In embodiments, the density of islets may be from about 10 to about 200 islets per ml of the medium, such as about 25 to 100 islets per ml of the medium, or 30 to 50 islets per ml of the medium. In embodiments, the culture of culture of cellular product may be maintained for periods of at least about 3 days, such as at least about one week or more.

In embodiments, plastic dishes, flasks, roller bottles, or microcarriers in suspension may be used to culture cellular product comprising islets according to the methods of the present disclosure. Suitable culture vessels may include, for example, multi-well plates, petri dishes, tissue culture tubes, flasks, roller bottles, and the like.

Various modifications to the culture system may be performed in order to reduce the difference between $pO_2$ gas and $pO_2$ cell. For example, convective oxygen transport in mechanically mixed or perfused vessels may be used, including stirring of and/or bubbling of oxygen through a culture medium. The cultures may be subject to in situ generation of oxygen using electrochemical hydrolysis of water. Alternatively or additionally, culture vessels having one or more sides, walls and/or bottom to which cells may attach and grow that comprise an oxygen permeable membrane can also be used. As used herein, an oxygen-permeable membrane is a membrane that has an oxygen permeability greater than that of a standard (e.g., polystyrene) culture dish. One example of an oxygen-permeable membrane is a fluoroethylene-propylene copolymer (FEP-TEFLON®) membrane. Culture vessels comprising this membrane are commercially available as LUMOX™ dishes (Greiner Bio-One, Munich). Another example of an oxygen-permeable membrane is a silicone rubber membrane, which is used in the Examples.

In embodiments, silicone rubber culture containers or vessels that comprise a silicone rubber membrane may be used. For example, the internal face of the vessel to which the cellular product comprising islets is in contact with is made of silicone rubber. The advantage of silicone rubber is its high permeability to gases such as oxygen. Examples of culture vessels that may be used are commercially available from, for example, Wilson Wolf Manufacturing Inc., MN. Further examples may include those that are described in U.S. Patent Application Publication No. 20080227176, herein incorporated by reference in its entirety. In still other embodiments, an insert of such oxygen permeable membranes may be placed in any of the above-described containers or culture vessels. Inserts of silicone rubber membranes are available from for example Wilson Wolf Manufacturing Inc., MN.

In embodiments, during the course of the present culturing method, the pancreatic islets that may comprise pancreatites prepared by the method of the present disclosure may be attached to or become attached to the substrate in contact with which they are cultured. In embodiments, the culturing method may be carried out in a vessel that provides or contains a suitable substrate that is compatible with mammalian cell tissue and is capable of accepting the attachment of the pancreatic islets that may comprise pancreatites to it. Suitable vessels therefore include tissue culture dishes, which, as commercially available, have their bottom surfaces covered with a coating that promotes the attachment of cellular product comprising islets thereto. Other culture vessels that provide or contain a suitable substrate surface may of course be employed. In embodiments, the method of the present disclosure is conducted as a stagnant culture, i.e. the culture and the culture medium are left in a quiescent state except for optional changes of the culture medium (which may be a liquid) at intervals. It would, however, be equally possible to conduct the method employing other forms of culturing in which the cellular product comprising islets undergoing culture are attached to a substrate immersed in a culture medium, which may be a liquid culture medium.

In embodiments, the present disclosure provides methods of transplanting pancreatic islets that may comprise pancreatites, said method comprising isolating cellular product comprising islets from a donor tissue, culturing the cellular product comprising islets in a culture medium to prepare pancreatic islets that may comprise pancreatites, and introducing the pancreatic islets, which may comprise pancreatites, into a recipient or host. In embodiments, the recipient or host is a patient in need of a transplant of insulin producing cells, for example, a patient having Type I diabetes. Thus, the disclosure also provides a method for treating diabetes mellitus, for example, Type I diabetes, comprising the steps of isolating cellular product comprising islets from a donor tissue, culturing the cellular product comprising islets in a culture medium to prepare pancreatic islets that may comprise pancreatites, and transplanting the pancreatic islets, which may comprise pancreatites, into a host, recipient or patient.

The pancreatic islets that may comprise pancreatites may be used to screen and evaluate insulinotropic compounds. Insulinotropic compounds may be evaluated by administering and/or adding such compounds to the pancreatic islets that may comprise pancreatites prepared by the method of the present disclosure for their ability to potentiate insulin secretion in the presence of glucose, and in the presence and absence of GLP-1. In addition, the pancreatic islets that may comprise pancreatites prepared by the method of the present disclosure may also be utilized to measure insulin content, to examine insulin biosynthesis, to test the effects of a compound on, for example, cAMP (e.g., Direct SPA Screening Biotrak Assay Kit, Amersham, Piscataway, N.J.), as well as to measure metabolites in islet cells (e.g., spectrometric or fluorometric enzyme assays, or any other method known to those skilled in the art). The pancreatic islets that may comprise pancreatites prepared by the method of the present disclosure may also be used to measure glucagon release. Hyperglucagonemia is a common phenomenon in Type 2 diabetes. The major physiological effect of glucagon is to increase hepatic glucose production. An enhancement of circulating glucagon levels in Type 2 diabetic patients contributes significantly to fasting hyperglycemia. Thus, inhibition of glucagon release or reduction of the glucagon effect on target tissue is another approach to treat diabetes. The pancreatic islets that may comprise pancreatites prepared by the method of the present disclosure may provide a robust method to measure glucagon release and its regulation by a variety of compounds.

The pancreatic islets that may comprise pancreatites prepared by the methods of the present disclosure may be used in a variety of applications. These include but are not limited to transplantation or implantation of pancreatic islets that may comprise pancreatites in vivo; screening cytotoxic compounds, allergens, growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

The pancreatic islets that may comprise pancreatites may be used in vitro to screen a wide variety of compounds, such as cytotoxic compounds, growth/regulatory factors, pharmaceutical agents, etc. To this end, the pancreatic islets that may comprise pancreatites are maintained in vitro and exposed to the compound to be tested. The activity of a cytotoxic compound can be measured by its ability to damage or kill the pancreatic islets that may comprise pancreatites in culture. This may readily be assessed by vital staining techniques. The effect of growth/regulatory factors may be assessed, e.g., by total cell counts, and differential cell counts. This may be accomplished using standard cytological and/or histological techniques including the use of immunocytochemical techniques employing antibodies that define type-specific cellular antigens. The effect of various drugs on pancreatic islets that may comprise pancreatites may be assessed.

Pancreatic islets that may comprise pancreatites may be administered to a subject by any means known to those of skill in the art. Suitable means of administration include, for example, intravenous, subcutaneous, via the liver portal vein, by implantation under the kidney capsule, or into the pancreatic parenchyma. In embodiments, the pancreatic islets that may comprise pancreatites may be administered to the subject alone or in combination with a formulation or substrate. The pancreatic islets that may comprise pancreatites may be in formulations suitable for administration, such as, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In embodiments, the pancreatic islets that may comprise pancreatites or formulation thereof may be administered, for example, by direct surgical transplantation under the kidney, intraportal administration, intravenous infusion, or intraperitoneal infusion.

In determining the effective amount of the pancreatic islets that may comprise pancreatites to be administered in the treatment or prophylaxis of conditions owing to diminished or aberrant insulin expression, the physician evaluates cell toxicity, transplantation reactions, progression of the disease, and the production of anti-cell antibodies. For administration, the pancreatic islets that may comprise pancreatites prepared by methods of the present disclosure may be administered in an amount effective to provide normalized glucose responsive-insulin production and normalized glucose levels to the subject, taking into account the side-effects of the cell type at various concentrations, as applied to the mass and overall health of the patient. In embodiments, administration may be accomplished via single or divided doses.

Examples are set forth hereinbelow and are illustrative of different compositions and conditions that can be utilized in practicing embodiments. All proportions are by weight unless otherwise indicated. It will be apparent, however, that the disclosure can be practiced with many types of compositions and can have many different uses in accordance with the disclosure above and as pointed out hereinafter. For example, these Examples will be readily recognized by those having ordinary skill in the art as also being applicable to isolating human islets because pig pancreas is an art-recognized model for human pancreas.

Pig pancreas is a useful model for at least because pigs are regarded as the most promising source of islets for future clinical xenografting. The special case of pancreas preservation prior to isolation of cellular product comprising islets is of high significance in view of both the worldwide interest in islet xenotransplantation may facilitate improved islet yields without compromising islet function.

Moreover, the consensus strategic plans recently published by the International Xenotransplantation Association for considering clinical trials of porcine islet products for type 1 diabetes emphasizes the need and importance of sterile, disease free environment for the source pigs and the products. To this end, the LIFEPORT® system provides a convenient sterile environment for transport of the source pancreas from the site of procurement to the islet processing facility. This approach is applied to the preservation and procurement of viable islets after hypothermic perfusion preservation of porcine pancreata because pigs are now considered the donor species of choice for xenogeneic islet transplantation for a number of compelling reasons (O'Neil, J. J. et al., The isolation and function of porcine islets from market weight pigs, Cell Transplant. 10:235-246; 2001).

The success of porcine pancreas hypothermic perfusion for islets isolation may strongly be influenced by the surgical procedure of organ procurement and pancreas cannulation for ex-vivo machine preservation. The development of porcine pancreas surgical recovery method has not been an obvious procedure. Initially, the lack of detailed pig pancreas anatomy documentation has led to improper organ vasculature preservation during pancreas procurement. Inadequate organ procurement has resulted in inconsistent and incomplete pancreas machine perfusion, thus low islet yield and viability.

Until recently, the anatomy of the pig pancreas was not well documented. Physiologically and topographically the pig and human pancreata are considered similar. The pancreas is an elongated retroperitoneal gland as shown in FIG. 1. In both pigs and humans, the pancreas head is closely related to the proximal duodenum, but for pigs the pancreatic duct opening is found on the duodenum distal and separate from the common bile duct (Swindle, M. M.; Smith, A. C. Comparative anatomy and physiology of the pig. Scand. J. Lab. Anim. Surg. 23:1-10; 1997). There are a variable number of vessels originating from the splenic, hepatic, gastroduodenal, superior mesenteric, and celiac arteries that on an individual basis have irregular configuration of blood supply to the pancreas. Commonly, blood to the head is supplied by the posterior and anterior arcades arising from the gastroduodenal and superior mesenteric arteries (FIG. 1). In pigs, the head does not surround the pancreaticoduodenal arteries and veins—the latter lie between the head and duodenum with the branches to the pancreas easily identifiable. The neck and the body of the pancreas are usually vascularized by the dorsal and inferior pancreatic arteries. The former can originate from the either the splenic, hepatic, or directly from the celiac arteries. The inferior pancreatic artery may begin from the superior mesenteric artery (SMA) under the neck of the pancreas and course toward the tail along the posterior inferior margin of the pancreatic surface in intimate contact with the gland. It can communicate with a varying number of splenic artery branches. The neck of the pancreas is also the site of the portal vein at the confluence of the splenic and superior mesenteric veins. The pancreas tail receives its blood supply mainly from the splenic artery.

In embodiments where the donor tissue (pancreas) may be perfused and/or attached the LIFEPORT® perfusion machine, all exposed arterial branches on the margin of gastroduodenal and hepatic sides of the pancreas should be meticulously identified and ligated to ensure uniform perfusion throughout the gland and allow the effluent to emerge only from the portal vein. A surgical approach that proved optimal for pancreas perfusion/preservation for islet isolation is described by Taylor, M. J., et al., in Hypothermic perfusion of pancreas: Emphasis on preservation prior to islet isolation. In: Lee, C. Y., ed., Organ perfusion preservation. Boston, Mass.: Artech House Publisher; 2010, which is hereby incorporated by reference in its entirety.

As described by Taylor et al., an exemplary surgical approach may include the following: 1. A team of two operators for pancreas procurement; 2. Follow surgical facility requirements for dress code and personal protection equipment; 3. Verify with the OR veterinary technician that the pig is intubated and under general anesthesia (i.e., ketamine 22 mg/kg, acepromazine 0.2 mg/kg, and atropine 0.025 mg/kg); confirm with the OR veterinary technician of pig anesthesia maintenance and proper ventilation; 4. Verify with the OR veterinary technician that all vital signs are monitored (ECG, heart rate, oxygen saturation level, body temperature, etc); 5. Verify that an electrical knife, a suction line and canisters are available. 6. Verify that the OR back field surgical table has been properly prepared (surgical instruments, lap sponges, gauze, cold saline, umbilical tape, etc.); 7. Verify that 2 L of cold Lactated Ringer's solution have been placed on ice; 8. Verify that an I.V. pole is available near the operating table and its height is appropriate for the gravity driven in-situ flushing of the organs (about 6 to about 6.5 feet); 9. Obtain permission from the OR veterinary technician to proceed with the surgery; 10. Minimize pancreas exposure to warm ischemia to 3 minutes, unless otherwise desired; 11. When permission has been granted, perform a midline incision from the xiphoid cartilage to just above the pelvis and expose the abdominal cavity; 12. Instruct the OR veterinary technician to administer heparin to the pig (about 150 U/kg), allow at least three minutes to pass before starting in-situ flushing; 13. Move and keep aside the bladder and the intestines (with the help of lap sponges) and identify the descending aorta; 14. Dissect, below the kidneys, a segment (about 3 cm) of the aorta apart from the surrounding tissue/vessels, place umbilical tape ties around the aortic segment; cut a small opening into the aorta between the two ties while the surgery assistant applies pressure on the aortic walls to prevent blood from squirting out; 15. Insert aortic cannula into the opening and tie it in place (make sure the umbilical tape tie is securely placed over the collar of the cannula); 16. Insert the two spikes of the irrigation set into the appropriate infusion ports of the two bags of Lactated Ringer solution (make sure the roller clamp is closed to prevent solution loss); 17. Hang the bags of Lactated Ringer solution on the I.V. pole and flush the irrigation set tubing to properly remove all the air; close the roller clamp; 18. Cross-clamp the inferior vena cava and the aorta above the diaphragm; 19. Connect the inlet opening of the cannula to irrigation set outflow port and open the roller clamp to initiate the gravity driven in-situ flushing; 20. Cut-open the inferior vena cava above the diaphragm, downstream from the clamp for blood outflow; 21. Immediately place plenty of ice inside the abdominal cavity around the pancreas and liver for organs maintenance/protection at low temperature; 22. Use the suction tubing and containers to collect the wash-out blood; 23. Make sure the solution flow from the bags, through the cannula into the aorta is not obstructed and that there is outflow from the inferior vena cava; 24. When empty, remove the bag of Lactated Ringer solution from the I.V. pole and hang the bag of SPS-1 solution (previously kept on ice), use only half of the SPS-1 solution volume to flush the organs; 25. Instruct the OR veterinary technician to euthanize the pig using a lethal dose of 5% sodium pentobarbital administered intravenously (accepted form of euthanasia according to the American Veterinary Medical Association Panel on Euthanasia (AVMA) guidelines) and complete in-situ flushing; 26. Transfer the second half of the SPS-1 solution bag to the pancreas transportation biohazard bag and place the latter on ice; 27. Carefully and rapidly (less than 15 minutes) proceed to expose and dissect apart the pancreas from the surrounding tissue and organs (add ice around the visceral organs as needed), make sure pancreas capsule and integrity are maintained; 28. Keep a segment of proximal duodenum (from near pylorus and inclusive of most the duodenum second descending part) attached to the pancreas head; make sure the duodenum segment includes the opening of the pancreatic duct (FIG. 1); 29. Ligate the splenic vein and artery prior to spleen detachment; 30. Keep an about 5 to about 7 cm long aortic segment attached to the pancreas for future organ cannulation; the aortic segment should include the openings of both superior mesenteric artery (SMA) and celiac trunk (CT); 31. Remove pancreas from the body, and with the aortic cannula attached, quickly wash off the blood from the pancreas outer surface using cold saline; immerse the pancreas in the SPS-1 solution inside the transportation bag; 32. Place the bag with the pancreas on ice, inside the pancreas cooler for transportation to the islet isolation laboratory.

In embodiments where the donor tissue (pancreas) may be perfused and/or attached the LIFEPORT® perfusion machine, exemplary methodology for pancreas cannulation for machine perfusion may include the following: 1. A team of two operators is recommended for pancreas cleaning and cannulation, 2. Perform pancreas cannulation at the isolation laboratory in order to reduce static cold ischemia damage prior to machine perfusion; 3. Minimize pancreas exposure to static cold ischemia to less than 2 hour, static cold ischemic time is the time elapsed from the initiation of in-situ flushing to the beginning of machine perfusion; 4. Transfer the pancreas from the transporting cooler to the stainless steel surgical tray; place the latter on ice and dispense about 20-30 mL of SPS-1 solution from the transporting bag into the tray to help keep the pancreas moist and cold; 5. Remove the aortic cannula; clean away all miscellaneous tissue while paying attention to maintaining pancreas integrity; identify and expose the SMA and CT vessels; 6. Dissect the aortic segment at midline to expose the orifices of SMA and CT, at this point the SMA and CT orifices should be clearly seen positioned apart on the aortic cuff (1.5 cm×4 cm); 7. Place and secure in place the appropriate size seal-ring cannula, the correct size should enclose both SMA and CT orifices without obstruction and clearly allow for their visualization through the top clear wall of the cannula; 8. Test for leaks; fill a 20 cc syringe with the solution to be used for perfusion, attach the syringe to one end of the cannula, remove the air inside the cannula and cap the other end of the cannula, gently infuse the solution into the pancreas and identify any leaks from exposed vessels; 9. Meticulously identify and ligate all exposed leaking arterial branches on the margin of gastroduodenal and hepatic sides of the pancreas (use umbilical tape and/or silk ties appropriately); 10. Cannulate the pancreatic duct; remove the needle from the surflo-winged infusion set and use its tubing as the duct cannula; using the micro-surgery scissors cut an opening into the pancreatic duct at its originating location on the duodenum and insert the cannula; secure the latter in place by tie suturing it to the duodenum wall; 11. Measure and record pancreas weight (subtract cannula weight), mass (subtract cannula mass), volume, circumference, and/or buoyancy.

The identification and tight ligation of all exposed vessels on the hepatic and gastroduodenal sides of the pancreas are of high importance. Usually about 12 to about 14 vessels are tied prior to perfusion to eliminate the possibility for a pathway of 'least resistance' for the flow throughout the organ and to allow the effluent to emerge only from the portal vein. Leaks from open exposed vessels compromise the uniformity of the organ perfusion that in turn can lead to pressure and temperature gradients across organ surface and suboptimal pancreas preservation.

Figure 2:
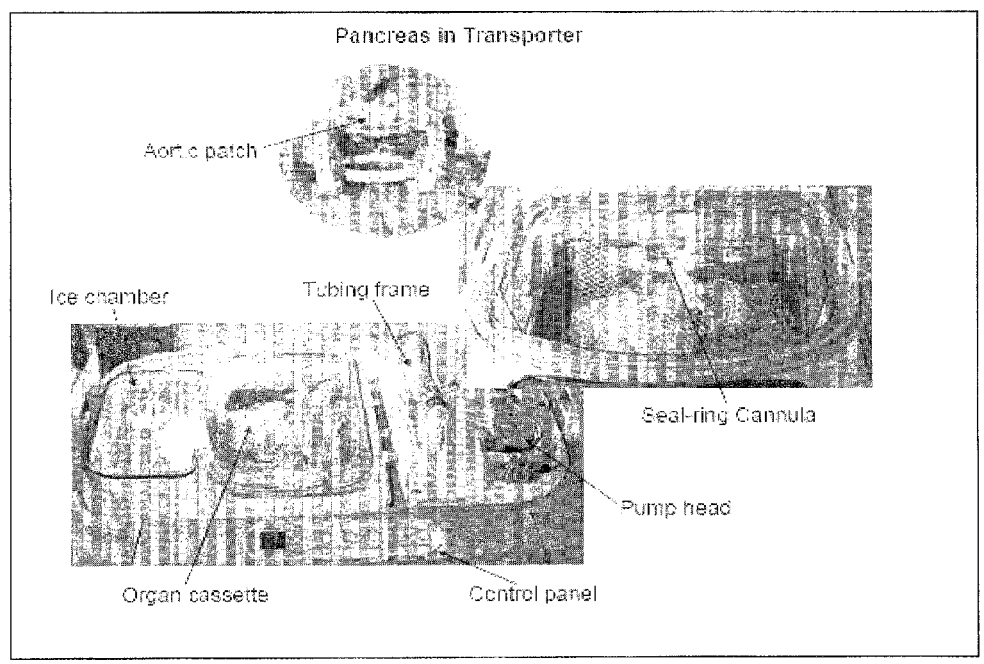
FIG. 2 includes photographs illustrating hypothermic perfusion preservation of a porcine pancreas on a LIFE-PORT® machine; the lower panel shows the principal features of the LIFEPORT®; the middle panel shows the details of a pig pancreas installed in the perfusion cassette and hooked up to the perfusion inlet line via a seal-ring cannula; this proprietary cannula allows simultaneous perfusion of the celiac trunk (CT) and superior mesenteric artery (SMA) by way of an aortic patch clamped in the seal-ring cannula (see circular inset); the inset photo shows the opening of the CT and SMA in the aortic patch (AP) which was exposed for viewing by opening the seal-ring cannula.

Exemplary methodology for the application of pancreas machine perfusion may include the following (FIG. 2): 1. Fill up the ice container with a mixture of ice and cold water (consult LifePort™ operation manual), place the container in the transporter main enclosure; 2. Place the organ cassette inside the cassette well, install the perfusion circuit tube frame on the pump deck and close the aluminum locking arm, connect the pressure sensor to the pressure transducer; 3. Press POWER to turn On the user controls of the transporter and follow the directions of the outer display to get the transporter ready for perfusion; 4. Add 1 L of cold perfusion solution to the organ cassette; set the infusion pressure to about 10 mmHg on the control panel, verify that the ice container temperature, as indicated by the outer display, is below about 8° C.; 5. Press WASH to start the pump and circulate the perfusate throughout the circuit; make sure all the air from the circuit is removed; 6. Place the pancreas (with the duodenum attached) inside the cassette, and position the organ cannula in the cannula mount of the cradle, connect the cannula inlet port to the infusion line and open the cannula outlet port; 7. Press PRIME to remove the air from the cannula and infusion line, and then cap the cannula; the latter will stop the flow and the pump based on the detected resistance; 8. Press STOP; press INFUSE to initiate the pancreas perfusion mode, watch for the pump to begin rotating and to increase its speed until the pressure set point is reached (e.g. about 10 mm Hg); 9. Ensure real time visualization and recording of flow parameters on both outer display and data station, the perfusion parameters as displayed on the outer panel are: pressure set point (systolic pressure, mmHg), flow rate (mL/min), resistance (mmHg/(mL/min)), temperature (° C., within the insulated cold section of transporter, i.e., ice container), to read the infusion temperature (° C.) and diastolic pressure (mmHg) press the scrolling arrows on the right side of the outer display to sequentially toggle through these additional parameters; 10. Allow pancreas perfusion for the desired amount of time, such as less than about 24 h (or in the range from about 4 h to about 24 h, such as about 8 h to about 16 h), or about 24 h or more, or in the range from about 24 h to about 48 h; stop the pump and save the data file (includes the dynamics of all perfusion parameters); 11. Remove the pancreas from the cassette; measure post-perfusion pancreas weight, mass, circumference, buoyancy, volume and record it; determine the level of fluid accumulation within the organ (edema %).

EXAMPLES

Figure 3:
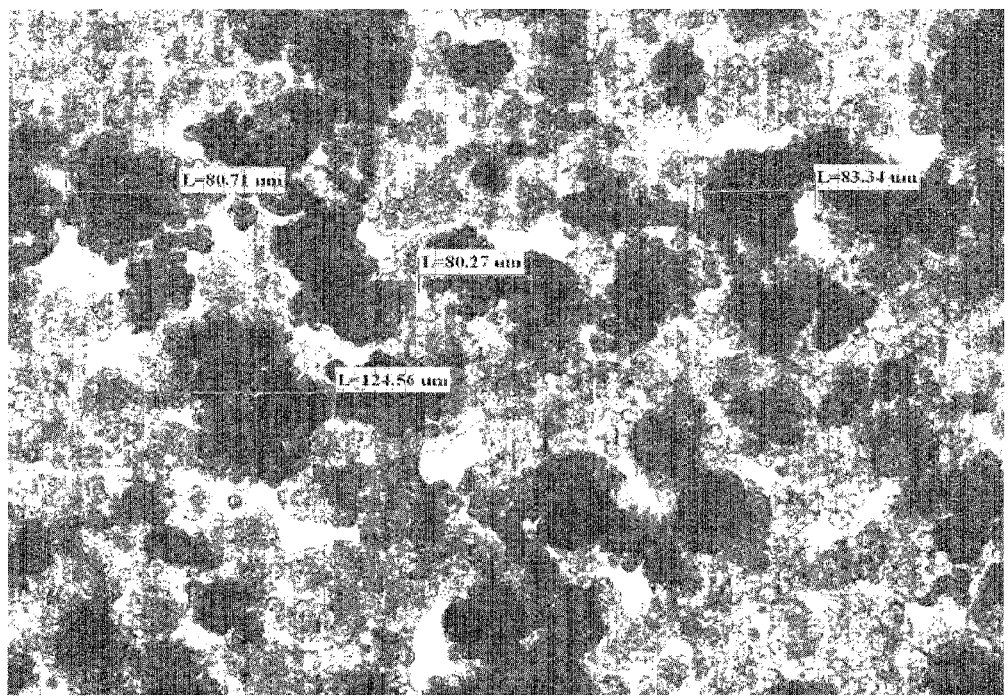
FIG. 3 is a light micrographs of non-cultured juvenile porcine islets post-isolation at day 0.
Figure 4:
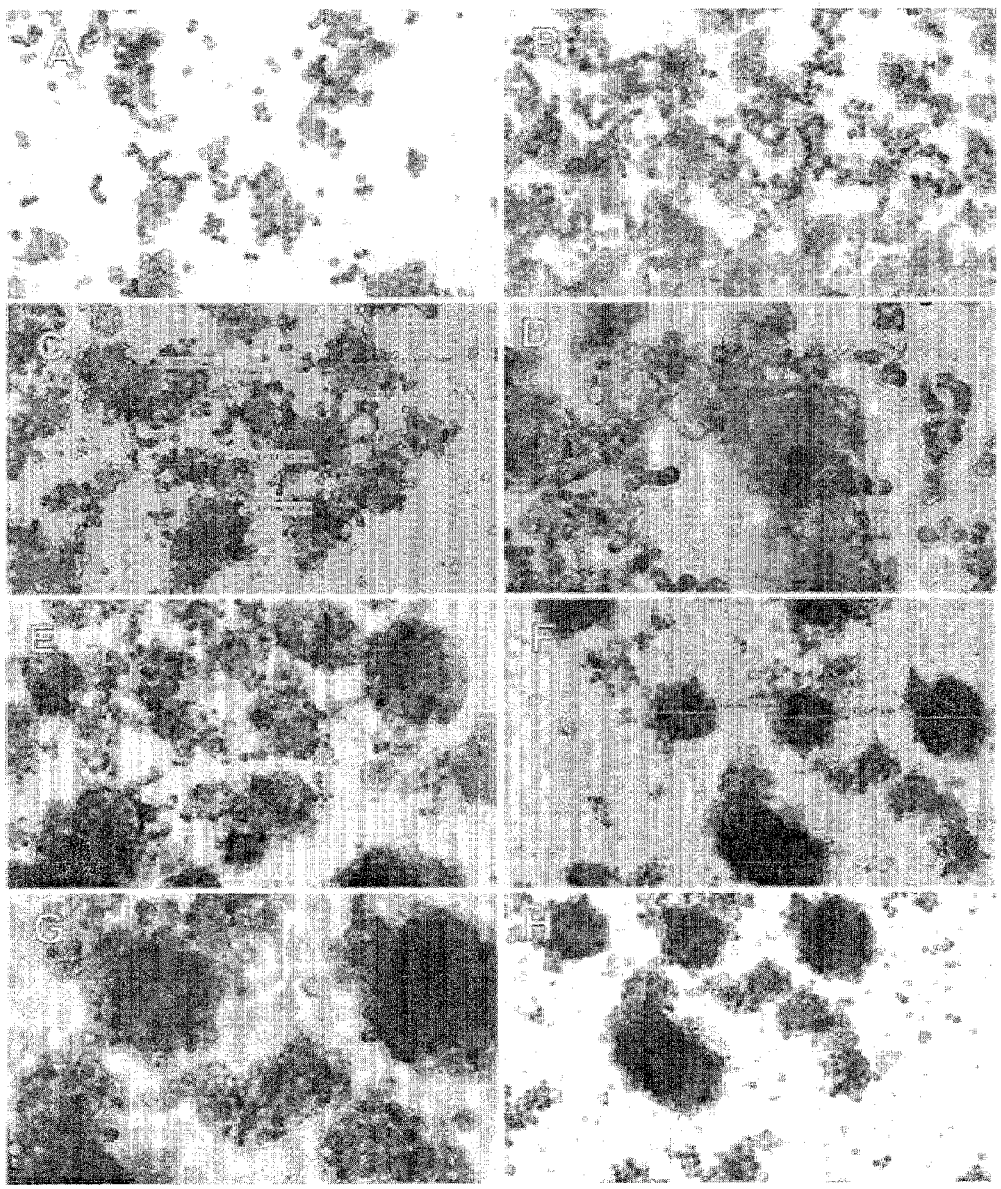
FIGS. 4A-H are light micrographs showing the cultured cellular product comprising islets at different stages in the culturing process, islets are identified by dithizone staining and appear purple-red in contrast to the unstained exocrine tissue which appears grey-brown, A=24 hours (×100), B=24 hours (×100), C=48 hours (×100), D=48 hours (×200), E=5 days (×100), F=6 days (×100), G=6 days (×200), H=6 days (×100)

Pancreases from juvenile pigs (<6 months old) were excised, flushed with preservation solution, stored hypothermically for 1 to 24 hours, distended by ductal infusion of a collagenase enzyme to dissociate the gland into acinar (exocrine) tissue and pancreatic islets (endocrine), and finally the digest was processed on a density gradient to purify the islets. The latter process was implemented such that complete purification of the islets was not attempted. FIG. 3 shows that the above process yielded 70-80% pure islets. The purity of the islets was assessed by calculating by monitoring (either visually and/or stereoscopically) the ratio of the area encompassed by the islets to the total area of exocrine tissue and endocrine tissue present in the culture medium. FIG. 4 shows the plasticity observed during post-isolation culture of the immature islets prepared from a juvenile pancreas after 24 hours hypothermic machine perfusion (HMP). The tissue was incubated at 37° C. in specialized Wilson-Wolfe flasks (Wilson Wolf Manufacturing Inc., MN) in which the tissue sits on the surface of a silicone membrane to facilitate oxygen exchange with the environment. Each panel of FIG. 4 shows the appearance of the endocrine (stained red with dithizone) and exocrine (unstained grey-brown) at various time points during culture for 1 week post-isolation—FIG. 4 (A-H): A: 24 hours (×100); B: 24 hours (×100); C: 48 hours (×100); D: 48 hours (×200); E: 5 days (×100); F: 6 days (×100); G: 6 days (×200); H: 6 days (×100).

Figure 5:
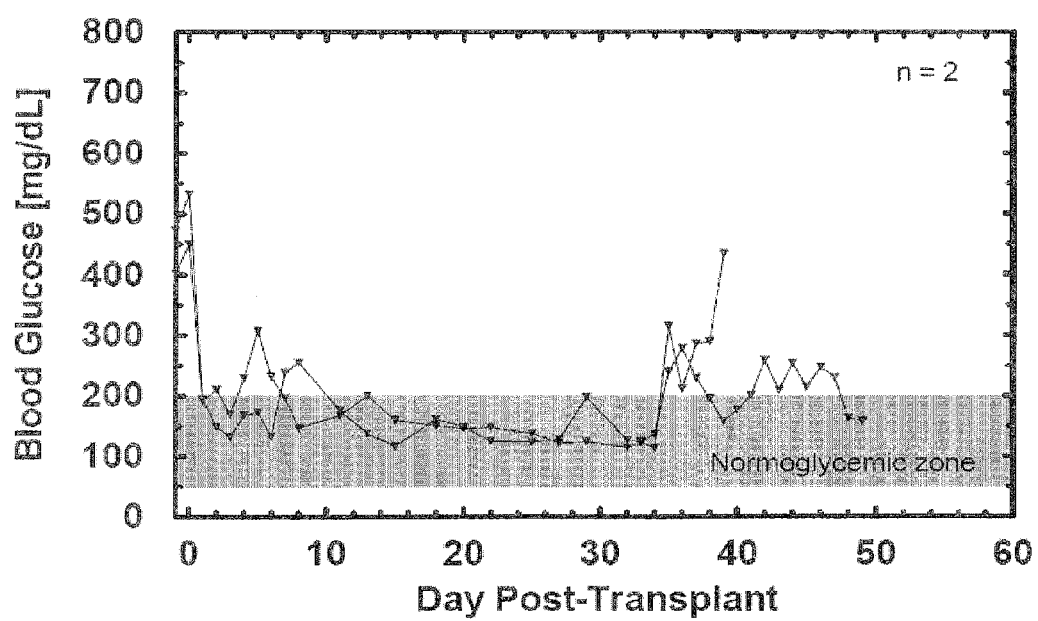
FIG. 5 represents data from viability tests in which nude mice were administered pig pancreatic islets comprising pancreatites isolated from a preserved pancreas after 24 hours of HMP perfusion.

Interestingly, the gross morphology of the islets changes during the first 24 hours in culture (compare looser more fragmented nature of the 24 h cultured islets in FIGS. 4A and 4B, compared with the "grape-like" clusters of islets on day 0 immediately post-isolation). The transition of the tissue from a loosely disaggregated appearance at 24 hours to more condensed aggregated structures comprising both exocrine and endocrine cells by day 6. This contrasts markedly with the typical behavior of islets from adult species, which maintain their islet individuality and post-isolation structure throughout culture. In cultures of adult islets the contaminating exocrine tissue tends to disintegrate and disappear by autolysis leaving an even purer preparation of individual islets. In contrast, the tissue from immature pigs appears to re-aggregate into larger new structures comprising endocrine and exocrine cells in coexistence as in the natural pancreas—hence the term "pancreatite." These structures were subsequently processed in a variety of in vitro and in vivo (FIG. 5) viability tests and demonstrated to be fully functional in terms of insulin secretion in response to glucose challenge. FIG. 5 shows that the diabetic condition of immunocompromised mice was cured by transplantation of porcine pancreatites placed under the kidney capsule. Further analysis by conventional histology will confirm the structural composition of these pancreatites.

What is claimed is:

1. A method of preparing pancreatic islets, comprising:
culturing pancreatic islets obtained from a donor pancreas ex vivo in the presence of a donor tissue material in a culturing medium comprising at least a detectable amount of acinar tissue obtained from the donor pancreas; wherein
the donor tissue material is produced by distending and dissociating a pancreas or
pancreas tissue
by ductal infusion of a collagenase enzyme, and
the islets are dispersed in the culture medium, and the islets are present in an amount less than about 70% and greater than about 20% of the total area of the acinar tissue and an endocrine tissue present in the culture medium, the amount of islets being calculated by the ratio of the area encompassed by the islets to the total area of acinar tissue and endocrine tissue present in the culture medium; and
forming pancreatites in the culture medium via aggregation of the acinar tissue and the dispersed islets; wherein
the islets were obtained from a donor selected from the group consisting of a non-adult donor and a juvenile donor,
the islets comprise immature islets, and
the culture medium is present on a gas permeable membrane.

2. The method of claim 1, further comprising isolating the islets from pancreas tissue by treating the pancreas tissue with a digestive enzyme.

3. The method of claim 1, wherein the culture medium is present in a polycarbonate gas permeable silicone membrane culture flask.

4. The method of claim 1, wherein the islets were obtained from a juvenile donor.

5. The method of claim 1, wherein the donor tissue material is obtained from a donor pancreas that was not the source of the islets.

6. The method of claim 1, wherein the donor tissue material and the islets are obtained from a single donor pancreas.

7. The method of claim 2, wherein after the islets are isolated from the pancreas tissue, the islets are combined with the donor tissue material.

8. The method of claim 7, wherein the donor tissue material and the islets are obtained from a single donor pancreas.

9. A method for preparing pancreatites, comprising:
treating donor tissue comprising pancreatic islets via digestion with an enzyme to obtain cellular product comprising islets and a detectable amount of exocrine tissue comprising acinar tissue;
seeding the cellular product comprising the islets and the detectable amount of exocrine tissue comprising acinar tissue into a culture medium to form a culture medium comprising dispersed islets; wherein
the islets are present in an amount less than about 60% and greater than about 20% of the total area of acinar tissue and endocrine tissue present in the culture medium, the amount of islets being calculated by the ratio of the area encompassed by the islets to the total area of acinar tissue and endocrine tissue present in the culture medium;
aggregating the exocrine tissue and the dispersed islets to form pancreatites in the culture medium; wherein
the islets were obtained from a donor selected from the group consisting of a non-adult donor and a juvenile donor,
the islets comprise immature islets, and
the culture medium is present on a surface of a gas permeable membrane.

10. The method of claim 9, wherein the pancreatites comprise endocrine cells and exocrine cells.

11. The method of claim 9, wherein the surface of a gas permeable membrane is a silicone membrane of a polycarbonate gas permeable silicone membrane culture flask.

* * * * *